United States Patent [19]

Brasseur

[11] Patent Number: 4,618,496

[45] Date of Patent: Oct. 21, 1986

[54] ANTIMICROBIAL PEAT MOSS COMPOSITION

[75] Inventor: Raynald Brasseur, Montreal, Canada

[73] Assignee: Johnson & Johnson, New Brunswick, N.J.

[21] Appl. No.: 631,271

[22] Filed: Jul. 16, 1984

[51] Int. Cl.$^4$ .............................................. A01N 65/00
[52] U.S. Cl. ..................................... 424/195.1; 424/28; 424/27; 71/90; 604/286; 604/369; 119/1
[58] Field of Search ................ 71/1, 11, 24, 27, 64.13, 71/90; 604/286, 369; 424/195.1; 119/1

[56] References Cited

U.S. PATENT DOCUMENTS 3,762,414 10/1973 Burnhill ............................... 604/369
3,918,452 11/1975 Cornfeld ......................... 604/286 X
4,042,372 8/1977 Harper .................................... 71/90

*Primary Examiner*—Ferris H. Lander
*Attorney, Agent, or Firm*—Jason Lipow

[57] ABSTRACT

A composition for inhibiting the growth of microorganisms comprising peat moss having substantively bound thereto an antimicrobial heterocyclic compound.

4 Claims, No Drawings

ANTIMICROBIAL PEAT MOSS COMPOSITION

BACKGROUND OF THE INVENTION

This invention relates to antimicrobial compositions and in particular relates to a composition useful in the manufacture of hygienic and health care products, particularly of the kind wherein body fluids are absorbed and retained and wherein control of microbial populations is desired. Such products may include for example, sanitary napkins, tampons, wound dressings, surgical sponges, diapers, bed liners and the like.

It has long ago been suggested that antimicrobial compositions and compounds be included in such body fluid absorbing products both for the purpose of inhibiting the growth of pathological microbes and for the purpose of inhibiting microbes, through their metabolical processes, from breaking down proteinaceous materials into odiferous or skin irritating compounds. Examples of such suggestions are U.S. Pat. Nos. 3,920,020; 4,034,084; 3,490,454; 3,172,817; 3,707,148; 3,340,875; and 2,837,462.

The art is also replete with teachings of various compounds having antimicrobial properties which could be incorporated into body fluid absorbent products. One class of such compounds which is particularly effective is the heterocyclic compounds such as those described by H. W. Rossmore in *Developments in Industrial Microbiology*, Volume 20, 1978, Chapter 4. Such compounds are already commercially available from various manufacturers and are sold in the form of powders, solutions and emulsions. They are used for a variety of purposes e.g., preservatives in paint latices, adhesives, various laundry products, metal working fluids, fiber lubricant systems, textile manufacturing processes, inks, and the like.

When attempting to incorporate these heterocyclic antimicrobial compounds into absorbent product wherein the absorbent is essentially wood pulp or other cellulosic fiberous material, it has been discovered that only a small quantity of antimicrobial agent is substantively bound to the cellulosic material (by substantive, it is meant capable of withstanding multiple washings with water). Accordingly, only an amount insufficient to render the absorbent product antimicrobial to the desired degree has remained with the product.

Accordingly, there is a need for a composition capable of substantively retaining antimicrobial compounds such as heterocyclic compounds for use in body fluid absorbent products.

SUMMARY OF THE INVENTION

In accordance with this invention, it has been discovered that a composition capable of inhibiting growth of a broad spectrum of microorganisms may be provided. Specifically, such composition comprises peat moss having substantively bound thereto an antimicrobial compound selected from the group consisting of antimicrobial heterocyclic compounds. Preferably, the peat moss is in the form of a board.

It has been discovered that in contrast to compositions comprising cellulosic material and antimicrobial compounds, by employing peat moss, the antimicrobial is substantively bound to the peat moss in quantities which are sufficient to render body absorbent products antimicrobial to a significant degree.

The heterocyclic compounds, in aqueous or other solvent solution may be applied to raw peat moss, refined peat moss or preferably to peat moss in board form. The latter form of the peat moss substrate is preferable in that it is most conveniently employed in absorbent products such as is taught in U.S. Ser. No. 377,532 now U.S. Pat. Nos. 4,507,122, 3/26/85 and 423,387 now U.S. Pat. No. 4,473,440, 9/25/84. The application process may simply comprise soaking the peat moss substrate in a solution of the antimicrobial compound and then drying. A wide range of antimicrobial compounds may be employed with the proviso that, for hygienic products, such compounds are non-toxic. In accordance with these teachings such products will have a wide range of antimicrobial activity with respect to bacteria and yeasts.

DETAILED DESCRIPTION OF THE INVENTION

In accordance with this invention, a composition is provided comprising an antimicrobial heterocyclic compound substantively bound to peat moss.

A wide variety of heterocyclic compounds are known to have antimicrobial properties and are well described in the above-referenced article by H. W. Rossmore. Broadly, such heterocyclic compounds are defined as compounds possessing a cyclic structure with at least two different kinds of atoms in the ring, the simplest of which is ethylene oxide, widely used as a sterilizing agent. The use of heterocyclic compounds for antimicrobial purpose is quite old in the art, beginning perhaps with the use of quinine from cinchona bark.

Of particular interest with respect to this invention are a variety of heterocyclic compounds now commercially available and including:

(a) 10,10' oxybisphenoxyarsine sold by the Ventron Corporation under the trademark "Durotex" and having the structure:

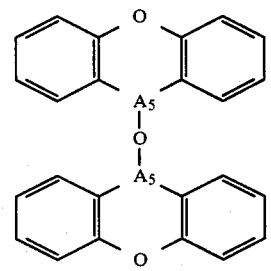

This compound is described in U.S. Pat. No. 3,288,674 and is soluble in alcohol and dispersable in water. The compound is sold in nonionic compositions as Durotex 7599, in anionic compositions as Durotex 7603, and in cationic compositions as Durotex 7604.

(b) Imidazolidinyl urea, sold by Sutton Laboratories, Inc. under the trademark Germall 115 and having the structure:

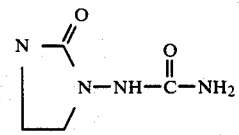

(c) 1-hexadecyl cetyl pyridinium chloride having the structure:

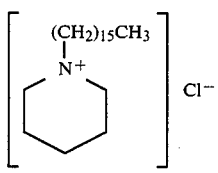

(d) 2n-octyl-4-isothiazolin-3-one, sold by the Rohm and Haas Company under the trademark Kathon LM and having the structure:

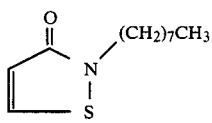

(e) sodium 2-mercapto benzo-thiazole sold in combination with sodium dimethyl dithiocarbamate; by the R. T. Vanderbilt Company under the trademark Vancide 51 and having the structure:

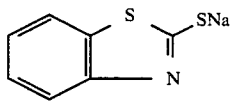

(f) cis-isomer of 1-(3-chloroalkyl)-3,5,7-triaza-1 azoniaadamantane chloride sold by the Dow Chemical company under the trademark Dowicil 200 and having the structure:

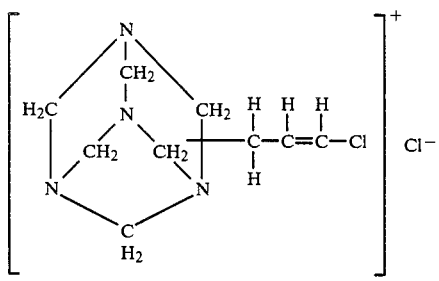

The Dowicil 200 is the compound of choice.

The peat moss substrate may be raw peat moss, preferably of the sphagnum type, that is capable of holding at least about 15 and preferably about 20 times its weight of water. Advantageously, the peat moss is screened to remove material such as roots and branches which are discarded. When the resultant peat moss is to be incorporated into absorbent products, it is best to further refine the raw peat moss by screening the same to eliminate the fines. The usable fraction is generally that portion remaining on a 100 mesh screen. Preferably, to insure discarding a larger portion of the peat fines, the portion remaining on a 75 mesh screen and more preferably that remain on about a 50 mesh screen is retained. For example, an excellent material can be utilized which is retained on a 48 mesh screen.

The refined peat moss may be subjected to other treatments such as bleaching or combining with other ingredients such as mechanical wood pulp, kraft pump or noncellulosic fibers such as polyester fibers. In a preferred form, the peat moss and other materials are formed into a water slurry and wet-laid into a low density board. This product is easily handled in processing equipment for manufacturing absorbent products.

The antimicrobial compound may be substantively bonded to the peat moss substrate by simply forming a solution of the compound in an appropriate solvent e.g., water or alcohol, and combining the substrate with the solution in a blender or by soaking the board form of the peat moss in the solution. Alternatively, in the case of the board, the compound may be added to the liquid in the board forming slurry. Solutions of the compound are effective at levels of as low as 0.01 percent by weight and may be utilized at concentration as high as 5 percent by weight or higher. Preferably solutions having a concentrate of at least 0.05 weight percent are employed but still more preferably, solutions having a weight percent of at least 0.1 are used. Advantageously, after combining the peat moss and antimicrobial solution, the composition is washed to remove excess antimicrobial solution.

As a result of this simple treatment, it has been discovered that the peat moss substrate having a heterocyclic compound solution applied thereto at a concentration of as low as 0.2 weight percent is capable of binding at least 5 mg of heterocyclic compound per gram of substrate. With solution concentrations of as high as 5 weight percent, the peat moss substrate can bind more than 50 mg of compound per gram of peat moss. This is particularly surprising in view of the fact that a wood pulp substrate will not bind a detectable quantity of compound at compound solutions of 0.2 percent by weight. At solution concentrations of 5 percent, by weight, wood pulp will bind less than 2 mg of compound per gram of substrate. By the term "bind" it is meant the quantity of compound detected by a distillation test as is set out below.

The invention may be best understood by consideration of the following examples.

EXAMPLE 1

To illustrate the enhanced antimicrobial activity of the composition of this invention, the peat moss substrate is compared to a wood pulp substrate. In each case five grams of the substrate material is blended in a Stomacher Laboratory Blender for 5 to 30 seconds with a 200 milliliter of an aqueous solution of the above-described Dowicil antimicrobial compound. The Dowicil material is present in the solution at a concentration of 0.2 percent by weight. The blended mixture is filtered on several layers of nonwoven fabric and washed five times with 100 ml of distilled water to remove the excess antimicrobial compound. The composition is tested for antimicrobial activity by spreading one ml of a suspension of each microorganism to be tested on an agar plate, placing the test sample over the agar and incubating. For bacterial microorganisms, suspensions employed were 1/1000 dilution of 24 hour culture and for fungal microorganism, suspensions employed were 1/100 dilution of seven day culture. Growth inhibition zones around the test sample are noted and rated on a scale of 0 to 4 with 0 representing no inhibition and 4 the highest activity.

The results are shown in Table 1 below wherein both the peat moss substrate sample tests and the wood pulp sample tests were repeated (A and B) at sequential time intervals.

| SAMPLE: | PEAT MOSS | | PULP | |
|---|---|---|---|---|
| | A | B | A | B |
| Microbial Species | | | | |
| Escherichia coli | 2 | 2 | 0 | 0 |
| Proteus mirabilis | 3 | 3 | 0 | 0 |
| Streptococcus faecalis | 3 | 3 | 1 | 1 |
| Pseudomonas aeruginosa | 2 | 2 | 0 | 0 |
| Bacillus subtilis | 3 | 3 | 0 | 0 |
| Staphylococcus aureus | 4 | 4 | 1 | 1 |
| Penicillium notatum | 1 | 0 | 1 | 0 |
| Aspergillus niger | 0 | 0 | 0 | 0 |
| Rhizopus oryzae | 0 | 0 | 0 | 0 |
| Mucor alterans | 0 | 0 | 0 | 0 |
| Cephalosporium chrysogenum | 4 | 4 | 2 | 0 |
| Trichophyton mentagrophytes | 3 | 3 | 2 | 1 |
| Penicillium expansum | 2 | 0 | 1 | 0 |
| Candida albicans | 0 | 0 | 0 | 0 |
| Trichosporon brassicae | 3 | 0 | 2 | 0 |
| Rhodotorula glutinis | 1 | 0 | 0 | 0 |
| Pichia pinus | 4 | 3 | 0 | 2 |
| Torulopsis apicola | 4 | 4 | 0 | 0 |
| Saccharomyces cerevisiae | 0 | 0 | 0 | 0 |
| TOTAL SCORE | 39 | 31 | 10 | 5 |

As is illustrated by the above Table 1, the peat moss compositions inhibited a higher number of species to a greater extent then did the wood pulp samples.

EXAMPLE 2

The method of Example 1 is repeated with the exception that a variety of heterocyclic compounds are employed in solutions of varying concentration as are set out in Table 2 below. Additionally, the mold microorganism Streptomyces griseus is added to the list of the 19 microorganisms tested in Example 1. The results are repeated in Table 2 below.

TABLE 2

| CONCENTRATION OF SOLUTION | NUMBER OF SPECIES INHIBITED | | | | |
|---|---|---|---|---|---|
| (wt %) | 0.2 | 0.1 | 0.5 | 0.02 | 0.01 |
| Heterocyclic Compound | | | | | |
| Kathon | 20 | 20 | 18 | 16 | 16 |
| Vancide | 15 | 14 | 12 | 12 | 8 |
| Dowicil 200 | 12 | 10 | 10 | 5 | 1 |
| Durotex 7599 | 20 | 20 | 20 | 20 | 20 |
| Durotex 7603 | 20 | 20 | 20 | 20 | 19 |
| Durotex 7604 | 20 | 20 | 20 | 20 | 20 |

As can be noted from the above Table, some activity is shown within the full range of concentrations investigated.

EXAMPLE 3

Surprisingly, it has been discovered that the composition of this invention, peat moss having heterocyclic compound substantively bound thereto, exhibit greater microbial inhibiting properties than the mere application of a corresponding solution of the heterocyclic compound itself. To illustrate this phenomenon, the procedure of Example 1 is repeated with respect to peat moss and Dowicil 200 samples wherein such samples comprise peat moss having applied thereto Dowicil 200 solutions at the various concentrations set out in Table 3 below. As a comparison, the mere corresponding solutions of Dowicil 200 are also tested for their microbial inhibiting properties. The antimicrobial test is that set out in Example 1, employing only the six bacterial species set out in that example. The results are reported below:

TABLE 3

| SOLUTION CONCENTRATION | NUMBER OF SPECIES INHIBITED | | | | | |
|---|---|---|---|---|---|---|
| (wt %) | 0.2 | 0.15 | 0.10 | 0.05 | 0.02 | 0.01 |
| Dowicil 200 solution | 4 | — | 1 | 0 | 0 | 0 |
| Peat Moss and Dowicil 200 | 6 | 6 | 6 | 6 | 1 | 0 |

As can be noted from the above, the compositions of this invention are more effective than the solution of heterocyclic compound used alone.

EXAMPLE 4

The following example contrasts the effectiveness of the compositions of this invention as compared with a wood pulp substrate when both are prepared using the technique of Example 1 and employing the heterocyclic antimicrobial compound Dowicil 200 at high solution concentrations. The microbial species tested using the method of Example 1 are the 20 species tested in Example 2. The results are given in Table 4, below:

TABLE 4

| SOLUTION CONCENTRATION | NUMBER OF MICROBIAL SPECIES INHIBITED | | |
|---|---|---|---|
| (wt %) | 1.0 | 2.0 | 5.0 |
| SUBSTRATE | | | |
| Peat Moss | 19 | 20 | 20 |
| Pulp | 13 | 14 | 16 |

As can be noted from this example, peat moss treated with a 1 percent Dowicil 200 solution is more effective than wood pulp treated with a solution of a concentration as high as 5 percent.

EXAMPLE 5

To illustrate the increased substantivity of heterocyclic antimicrobial compounds to peat moss as contrasted to that of wood pulp, the following procedure is performed. Samples of wood pulp, raw peat moss, and peat moss board (containing 80% peat moss of 8 to 40 mesh, 10% kraft pulp and 10% ground wood pulp) are all treated with variously concentrated solutions of the Dowicil 200 antimicrobial compounds using the procedure of Example 1. One gram of each sample is placed in a distillation flask with 100 ml of distilled water and 4 ml of concentrated sulfuric acid. The mixture is boiled and approximately 65 ml of water are distilled and transferred to a 100 ml volumetric flask. The volume is adjusted to 100 ml with fresh distilled water. Five ml of this solution is transferred to a test tube with 5 ml of an acetylacetone solution (75 grams ammonium acetate, 1.5 ml concentrated acetic acid, 1 ml acetylacetone, completed to 500 ml with distilled water). The tube is heated at 40° C. for 30 minutes and then cooled at room temperature for an additional 30 minutes. The absorbency is read in a spectrophotometer at 412 nm against a blank which blank comprises a water and acetyl acetone mixture treated similarly to the experimental samples. The results are converted to mg of heterocyclic compound per gram of substrate using a calibration curve obtained by testing Dowicil solutions of known concentrations.

The results of these tests are reported in Table 5 below:

TABLE 5

| SOLUTION CONCENTRATION | MG DOWICIL 200 PER GRAM OF SUBSTRATE | | |
| --- | --- | --- | --- |
| (wt %) | 0.2 | 2.0 | 5.0 |
| SUBSTRATE | | | |
| Pulp | 0 | 0.14 | 1.2 |
| Raw peat moss | 13 | 32 | 54 |
| Peat moss board | 9.7 | 48 | 70 |

EXAMPLE 6

To further illustrate the preferential binding of the heterocyclic compounds to peat moss as contrasted to wood pulp, the following is done. Samples of pulp and peat moss board are treated with various concentrations of the Dowicil 200 solutions in accordance with the method of Example 1. The samples are then treated to varing numbers of wash steps with 500 ml per wash of distilled water. The distillation test described in Example 5 is then utilized to determine the weight of heterocyclic compound retained per gram of substrate. The results are reported below in Table 6.

TABLE 6

| DOWICIL 200 CONCENTRATION | | RETAINED MG DOWICIL 200/ GRAM SUBSTRATE | | |
| --- | --- | --- | --- | --- |
| (wt %) | | 0.2 | 2.0 | 5.0 |
| SUBSTRATE | NO. OF WASHES | | | |
| PULP | 5 | 1.8 | 3.8 | 6.4 |
| | 10 | 0.8 | 0.9 | 0.6 |
| | 20 | 0.0 | 0.1 | 0.4 |
| Peat moss Board | 5 | 7.5 | 39 | 56 |
| | 10 | 6.0 | 23 | 40 |
| | 20 | 2.8 | 19 | 21 |

EXAMPLE 7

To illustrate the stability of the compositions of this invention peat moss samples are treated with 0.2 percent by weight solutions of various heterocyclic compounds in accordance with the method of Example 1. A portion of such samples are tested for antimicrobial properties using the method of Example 1 and the six bacteria species of that example. A second portion of such treated samples are dried and kept at room temperature for 34 days. This second portion is again tested for antimicrobial activity with respect to the six bacteria species. The results are reported in Table 7, below.

TABLE 7

| HETEROCYCLIC COMPOUND | NUMBER OF SPECIES INHIBITED | |
| --- | --- | --- |
| | Day 0 | Day 34 |
| Dowicil 200 | 6 | 5 |
| Kathon | 6 | 6 |
| Vancide | 4 | 2 |
| Durotex | 6 | 6 |

It can be noted that the activity remains essentially constant with time.

I claim:

1. A process for providing a composition for inhibiting the growth of microorganisms comprising:
   soaking peat moss in a solution comprising from 0.01 to 5.0 percent, by weight of an antimicrobial heterocyclic compound;
   removing excess solution and
   washing said treated peat moss to remove non-substantively bound heterocyclic compound while retaining at least five mg of substantively bound heterocyclic compound per gram of peat moss.

2. The method of claim 1 wherein said heterocyclic compound is selected from the group consisting of 10,10' oxybisphenoxyarsine; imidazolidinyl urea; 1-hexadecyl pyridinium chloride; 2n-octyl-4-isothiazolin-3-one; sodium 2-mercapto benzo-thiazole; or the cis-isomer of 1-(3-chloroalkyl)-3,5,7triaza-1-azoniaadamantane chloride.

3. The method of claim 1 wherein said peat moss is raw peat moss.

4. The method of claim 1 wherein said peat moss is in board form.

* * * * *